US012514340B2

(12) United States Patent
Xia et al.

(10) Patent No.: US 12,514,340 B2
(45) Date of Patent: Jan. 6, 2026

(54) MAGNETIC BUCKLE STRUCTURE FOR KNEE-JOINT BRACE AND KNEE-JOINT BRACE HAVING SAME

(71) Applicants: VINCENT MEDICAL (DONG GUAN) MANUFACTURING CO., LTD, Dongguan (CN); VINCENT MEDICAL (DONG GUAN) TECHNOLOGY CO., LTD, Dongguan (CN); REHAB-ROBOTICS COMPANY LIMITED, Kowloon (HK)

(72) Inventors: Mingjun Xia, Dongguan (CN); Wei Liang, Dongguan (CN); Guofu Fu, Dongguan (CN); Jialin Cai, Dongguan (CN); Peiyong Xu, Dongguan (CN); Yongjian Chen, Dongguan (CN)

(73) Assignees: VINCENT MEDICAL (DONG GUAN) MANUFACTURING CO., LTD, Guangdong (CN); VINCENT MEDICAL (DONG GUAN) TECHNOLOGY CO., LTD, Guangdong (CN); REHAB-ROBOTICS COMPANY LIMITED, Hong Kong (CN)

( * ) Notice: Subject to any disclaimer, the term of this patent is extended or adjusted under 35 U.S.C. 154(b) by 243 days.

(21) Appl. No.: 18/547,658

(22) PCT Filed: Mar. 23, 2023

(86) PCT No.: PCT/CN2023/083439
§ 371 (c)(1),
(2) Date: Aug. 23, 2023

(87) PCT Pub. No.: WO2023/179722
PCT Pub. Date: Sep. 28, 2023

(65) Prior Publication Data

US 2025/0000215 A1 Jan. 2, 2025

(30) Foreign Application Priority Data

Mar. 25, 2022 (CN) ......................... 202210300786.3

(51) Int. Cl.
*A44B 11/25* (2006.01)
*A41F 1/00* (2006.01)
*A61F 5/01* (2006.01)

(52) U.S. Cl.
CPC .............. *A44B 11/25* (2013.01); *A41F 1/002* (2013.01); *A61F 5/0123* (2013.01)

(58) Field of Classification Search
CPC .. A61F 5/0123; A61F 5/02; A61F 5/32; A61F 2005/0137; A61F 2005/0165;
(Continued)

(56) References Cited

U.S. PATENT DOCUMENTS

2005/0240135 A1* 10/2005 Hoffmeier ............. A61F 5/0123 602/26
2010/0130899 A1 5/2010 Chao
(Continued)

FOREIGN PATENT DOCUMENTS

CN 102481034 A 5/2012
CN 207429243 U 6/2018
(Continued)

OTHER PUBLICATIONS

International Search Report from the related PCT application has been provided.

*Primary Examiner* — Daniel A Miller
(74) *Attorney, Agent, or Firm* — MUNCY, GEISSLER, OLDS & LOWE, P.C.

(57) ABSTRACT

A magnetic buckle structure for a knee-joint brace and a knee-joint brace having the same. The magnetic buckle structure for the knee-joint brace includes a joint brace body, a lower magnetic buckle arranged on the joint brace body,
(Continued)

and an upper magnetic buckle arranged on the lower magnetic buckle and magnetically connected to the lower magnetic buckle. Through the arrangement of the upper magnetic buckle and the lower magnetic buckle, a bandage of the knee-joint brace can be magnetically fixed or replaced, whereby being convenient for a user to wear and remove the knee-joint brace.

10 Claims, 3 Drawing Sheets

(58) Field of Classification Search

CPC . A61F 2005/0174; A44B 11/25; A44B 11/06; A44B 11/28; A44B 11/2596; A44B 11/2588; A44B 11/258; A44B 11/2546; A44B 11/2534; A41F 1/002

USPC .......................................................... 602/26

See application file for complete search history.

(56) References Cited

U.S. PATENT DOCUMENTS

| | | | |
|---|---|---|---|
| 2013/0097824 A1 | 4/2013 | Chadwick | |
| 2020/0154804 A1 * | 5/2020 | Huang .................. | A44B 11/28 |

FOREIGN PATENT DOCUMENTS

| | | |
|---|---|---|
| CN | 207492844 U | 6/2018 |
| CN | 109549766 A | 4/2019 |
| CN | 213430890 U | 6/2021 |
| CN | 113580101 A | 11/2021 |
| CN | 114869700 A | 8/2022 |
| KR | 20110026543 A | 3/2011 |
| KR | 20190058083 A | 5/2019 |
| TW | 554683 U | 9/2003 |

* cited by examiner

MAGNETIC BUCKLE STRUCTURE FOR KNEE-JOINT BRACE AND KNEE-JOINT BRACE HAVING SAME

TECHNICAL FIELD

The present disclosure relates to the technical field of rehabilitation and sports equipment, more particularly to a magnetic buckle structure for a knee-joint brace and a knee-joint brace having the same.

BACKGROUND

Knee joint is one of the joints in the human body that has a high load-bearing capacity and a complex structure. Knee joint diseases often occur in daily life, leading to limited human movement and seriously reducing the quality of life. In order to alleviate the damage of the knee joint diseases to the human body and improve the quality of life, a knee-joint brace is provided in the existing technologies, with which a support structure (such as a support arm) is arranged on the periphery of the knee joint to assist in supporting the knee joint associated bones, whereby assisting in fixing and supporting the knee joint. Therefore, the knee-joint brace can provide great protection and support for those people with knee joint discomfort, can reduce the pain and discomfort of the knee joints, and can provide walking support to certain extent for those people with walking disabilities, thereby reducing the condition of limited human movement and improving the quality of their lives.

However, for most of those patients with knee-joint diseases, their self-care abilities are greatly limited, and they often have problems in wearing and removing the knee-joint braces.

Therefore, the existing technologies have drawbacks and deficiencies and need to be further improved and developed.

SUMMARY

In view of the drawbacks of the existing technologies, the present disclosure aims to provide a magnetic buckle structure for a knee-joint brace and a knee-joint brace having the same, with the purpose of solving the problems in the existing technologies that the knee-joint brace is inconvenient to wear and remove.

The present disclosure solves the technological problems employing the following technical solution. A magnetic buckle structure for a knee-joint brace includes:

- a joint brace body;
- a lower magnetic buckle arranged on the joint brace body; and
- an upper magnetic buckle arranged on the lower magnetic buckle and magnetically connected to the lower magnetic buckle.

Further, the lower magnetic buckle includes:

- a lower magnetic buckle body integrally formed with the joint brace body;
- an upper magnetic buckle connection end arranged on an upper end surface of the lower magnetic buckle body along a height direction; and
- a lower magnet fixing end arranged on a lower end surface of the lower magnetic buckle body along the height direction.

Further, the upper magnetic buckle connection end includes:

- an upper magnetic buckle fitting part arranged on the upper end surface of the lower magnetic buckle body along the height direction; and
- a transverse baffle wall arranged on the upper magnetic buckle fitting part, and the upper magnetic buckle fitting part including a first groove, a first limit step and a second groove that are arranged in sequence;
- a first vertical baffle wall arranged on one end of the transverse baffle wall;
- a second vertical baffle wall arranged on the other end of the transverse baffle wall and symmetrical to the first vertical baffle wall; wherein
- the first vertical baffle wall and the second vertical baffle wall are gradually increased in height along one end close to the transverse baffle wall.

Further, one ends of the first vertical baffle wall and the second vertical baffle wall away from the transverse baffle wall are both provided with a limit buckle, and the limit buckle includes:

- a main body clamping bar arranged angled with the upper magnetic buckle fitting part and inclined toward the transverse baffle wall; and
- a limit clamping tooth arranged on one end of the main body clamping bar away from the upper magnetic buckle fitting part and facing the transverse baffle wall.

Further, the lower magnet fixing end includes a lower magnet fixing groove and a plurality of reinforcement ribs arranged on the periphery of the lower magnet fixing groove; and a magnet is arranged inside the magnet fixing groove.

Further, the upper magnetic buckle includes:

- an upper magnetic buckle body;
- an upper magnet fixing chamber arranged on the upper magnetic buckle body;
- a buckling limit part arranged at an area of the upper magnetic buckle body corresponding to the limit clamping tooth; and
- an assembly limit part arranged at an area of the upper magnetic buckle body close to the first groove.

Further, an edge of the upper magnetic buckle body corresponding to the first vertical baffle wall and the second vertical baffle wall, on one side along a height direction, is arranged as an arc shape.

Further, the buckling limit part includes:

- a main body clamping bar receding section clamped on the main body clamping bar; and a limit baffle clamped on the limit clamping tooth.

Further, the assembly limit part is arranged as a convex plate structure that is clamped to the second groove.

The present disclosure solves the technical problems employing another technical solution as follows. A knee-joint brace includes the magnetic buckle structure for the knee-joint brace described above.

The present disclosure provides a magnetic buckle structure for a knee-joint brace and a knee-joint brace having the same. The magnetic buckle structure for the knee-joint brace includes a joint brace body, a lower magnetic buckle arranged on the joint brace body, and an upper magnetic buckle arranged on the lower magnetic buckle and magnetically connected to the lower magnetic buckle. It is understandable that through the arrangement of the upper magnetic buckle and the lower magnetic buckle, a bandage of the knee-joint brace can be magnetically fixed or replaced, whereby being convenient for a user to wear and remove the knee-joint brace.

Figure 1:
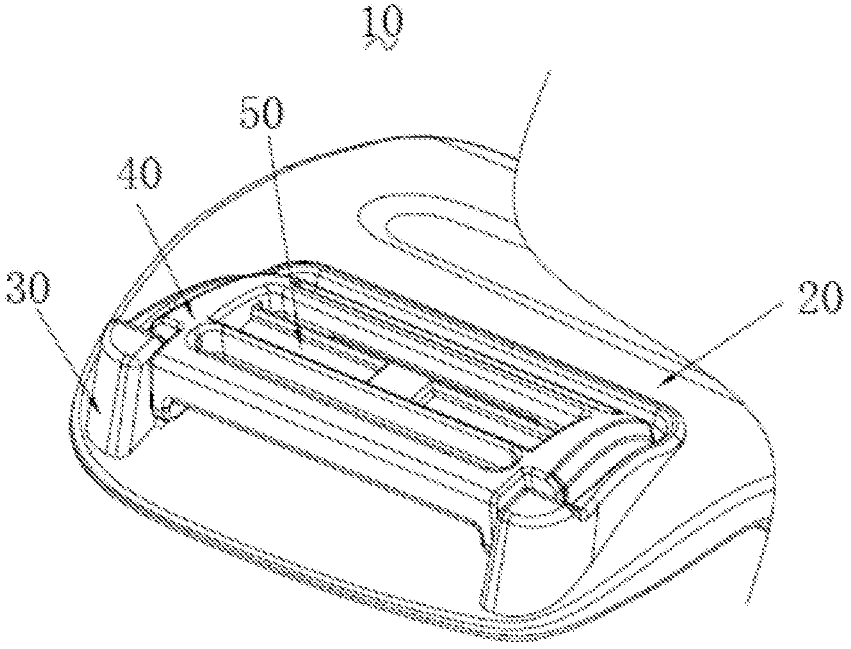
FIG. 1 is a perspective structure diagram of a magnetic buckle structure for a knee-joint brace according to the present disclosure.

Designators on the drawings are as described below:

10, a magnetic buckle structure for a knee-joint brace; 20, a joint brace body; 30, a lower magnetic buckle; 40, an upper magnetic buckle; 50, an S-pole magnet; 60, an N-pole magnet; 31, a lower magnetic buckle body; 32, an upper magnetic buckle connection end; 33, a lower magnet fixing end; 321, an upper magnetic buckle fitting part; 322, a transverse baffle wall; 323, a first vertical baffle wall; 324, a second vertical baffle wall; 325, a limit buckle; 3211, a first groove; 3212, a first limit step; 3213, a second groove; 3251, a main body clamping bar; 3252, a limit clamping tooth; 331, a lower magnet fixing groove; 332, a reinforcement rib; 41, an upper magnetic buckle body; 42, an upper magnet fixing chamber; 43, a buckling limit part; 44, an assembly limit part; 45, a bandage spacing; 431, a main body clamping bar receding section; and 432, a limit baffle.

DETAILED DESCRIPTION OF THE EMBODIMENTS

To make the purpose, the technical solution and the advantages of the present disclosure better understood, the present disclosure is described below in further detail in conjunction with specific embodiments by reference to the drawings. It should be understood that the specific embodiments described below are merely to illustrate, but to limit, the present disclosure.

In the description of the present disclosure, it is to be understood that the orientation or position relations indicated by such terms as "central", "longitudinal", "transverse", "above", "below", "front", "rear", "left", "right", "vertical", "horizontal", "top", "bottom", "inside", "outside", etc. are based on the orientation or position relations shown in the drawings, and are merely for conveniently describing the present disclosure and simplifying the description, rather than indicating or implying that the device or element must have the specific orientation and be constructed and operated according to the specific orientation. Therefore, they should not be construed as a limitation on the present disclosure. In addition, terms "first", "second" are merely for the purpose of description, but should not be understood as the indication or implication of relative importance or as the implicit indication of the quantity of the designated technical features. Therefore, features defined by "first" and "second" may specifically or implicitly include one or more such features. In the description of the present disclosure, unless otherwise stated. "a plurality of" means two or more than two.

In the description of the present disclosure, unless otherwise specifically stated and defined, terms such as "mounted", "interconnected", "connected", etc. should be interpreted expansively. For example, they may be fixed connection, also may be detachable connection, or integration; may be mechanical connection, also may be electrical connection; may be direct connection, also may be indirect connection through an intermediate, and may be internal communication between two elements. The ordinary skill in this field can understand the specific implication of the above terms in the present disclosure in accordance with specific conditions.

Knee joint is one of the joints in the human body that has a high load-bearing capacity and a complex structure. Knee joint diseases often occur in daily life, leading to limited human movement and seriously reducing the quality of life. In order to alleviate the damage of the knee joint diseases to the human body and improve the quality of life, a knee-joint brace is provided in the existing technologies, with which a support structure (such as a support arm) is arranged on the periphery of the knee joint to assist in supporting the knee joint associated bones, whereby assisting in fixing and supporting the knee joint. Therefore, the knee-joint brace can provide great protection and support for those people with knee joint discomfort, can reduce the pain and discomfort of the knee joints, and can provide walking support to certain extent for those people with walking disabilities, thereby reducing the condition of limited human movement and improving the quality of their lives. However, for most of those patients with knee-joint diseases, their self-care abilities are greatly limited, and they often have problems in wearing and removing the knee-joint braces. The present disclosure provides a magnetic buckle structure for a knee-joint brace and a knee-joint brace having the same in view of the problems in the existing technologies that the knee-joint brace is inconvenient to wear and remove. Through the arrangement of the upper magnetic buckle and the lower magnetic buckle, a bandage of the knee-joint brace can be magnetically fixed or replaced, whereby being convenient for a user to wear and remove the knee-joint brace. The following embodiments can be referred to for specific details.

Figure 2:
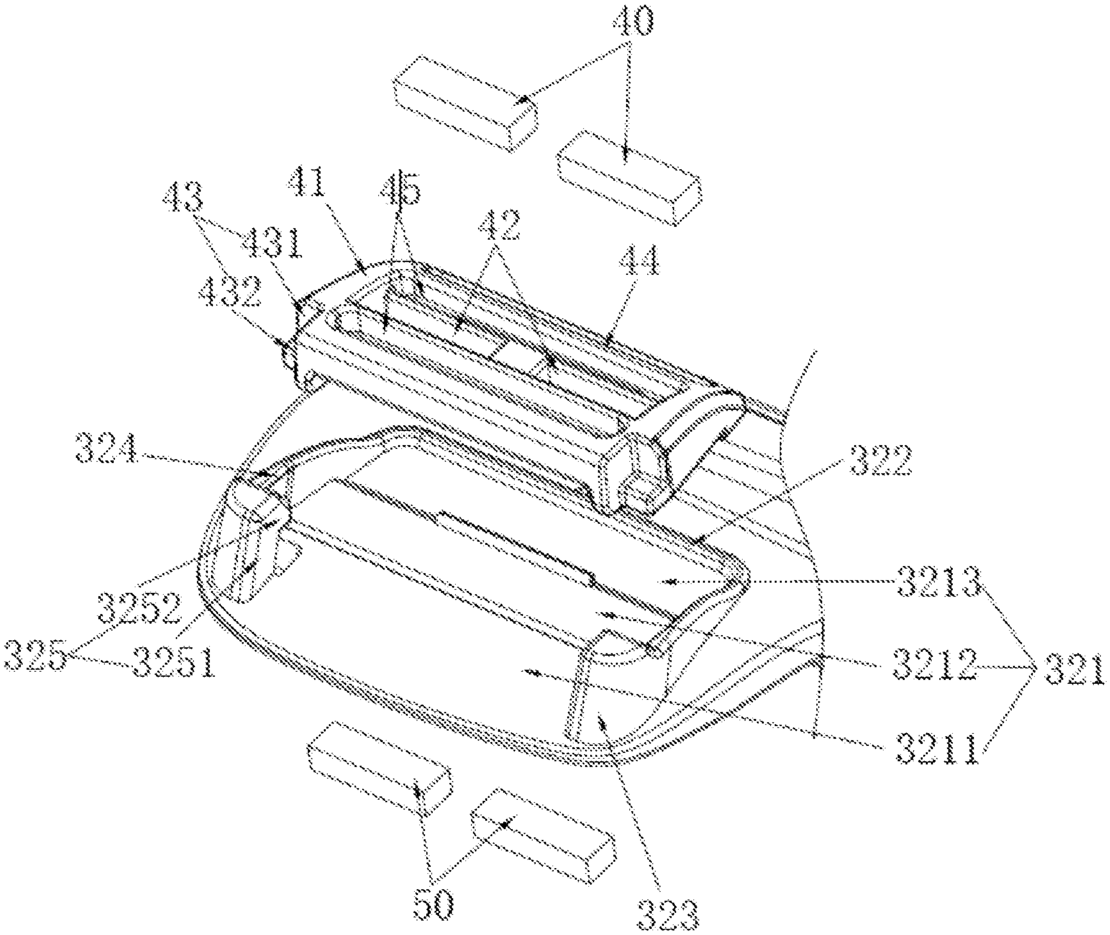
FIG. 2 is a perspective exploded diagram of a magnetic buckle structure for a knee-joint brace according to the present disclosure.
Figure 3:
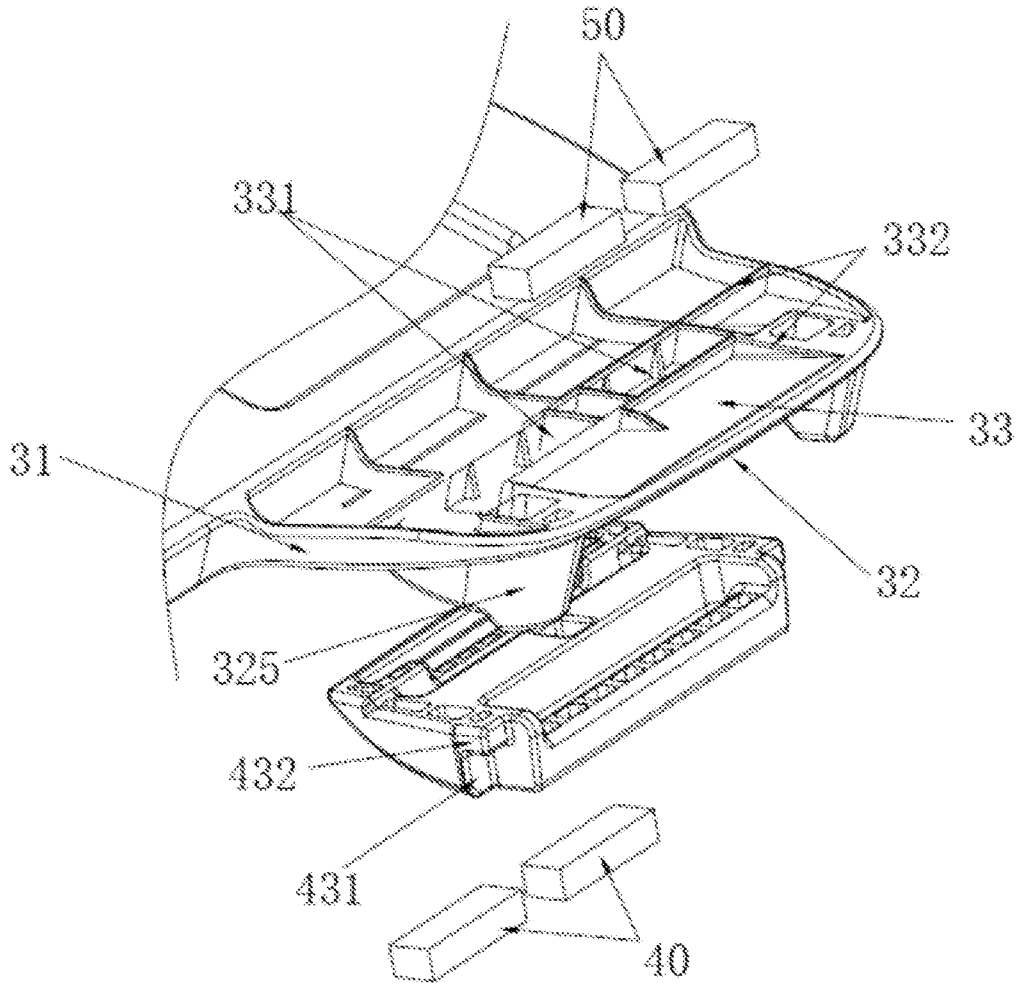
FIG. 3 is a perspective exploded diagram of a magnetic buckle structure for a knee-joint brace according to the present disclosure from another angle of view.

Referring to FIG. 1 to FIG. 3, a first embodiment of the present disclosure provides a magnetic buckle structure 10 for a knee-joint brace, including a joint brace body 20, a lower magnetic buckle 30 and an upper magnetic buckle 40. The lower magnetic buckle 30 is arranged on the joint brace body 20. The upper magnetic buckle 40 is arranged on the lower magnetic buckle 30 and magnetically connected to the lower magnetic buckle 30.

It is understandable that through the arrangement of the upper magnetic buckle 40 and the lower magnetic buckle 30 on the joint brace body, the knee-joint brace body 20 can be fixed with the assistance of the magnetic buckles. When the upper magnetic buckle 40 and the lower magnetic buckle 30 are magnetically connected, the knee-joint brace body 20 is preliminarily fixed, then the knee-joint brace can be tied or tightened conveniently. When to remove the knee-joint brace, the upper magnetic buckle 40 is separated from the lower magnetic buckle 30 before untying the knee-joint brace. It is greatly convenient to wear and remove the knee-joint brace. It is to be noted that the lower magnetic buckle 30 is integrally formed with the joint brace body 20, that is, the lower magnetic buckle 30 is a fixed magnetic buckle, while the upper magnetic buckle 40 is a moveable magnetic buckle.

In some other embodiments, the lower magnetic buckle 30 includes: a lower magnetic buckle body 31, an upper magnetic buckle connection end 32 and a lower magnet fixing end 33. The lower magnetic buckle body 31 is integrally formed with the joint brace body 20. The upper magnetic buckle connection end 32 is arranged on an upper end surface of the lower magnetic buckle body 31 along a height direction. The lower magnet fixing end 33 is arranged on a lower end surface of the lower magnetic buckle body 31 along a height direction.

It is understandable that the lower magnetic buckle body 31 is integrally formed with the joint brace body 20, thus guaranteeing the fastening function between the lower magnetic buckle 30 and the upper magnetic buckle 40. By arranging the magnet fixing end and the upper magnetic buckle connection end 32 on two end surfaces of the lower magnetic buckle body 31 respectively, a user can operate the magnetic buckle structure 10 of the knee-joint brace more conveniently.

In some other embodiments, the upper magnetic buckle connection end 32 includes: an upper magnetic buckle fitting part 321, a transverse baffle wall 322, a first vertical baffle wall 323 and a second vertical baffle wall 324. The upper magnetic buckle fitting part 321 is arranged on an upper end surface of the lower magnetic buckle body 31 along a height direction. The transverse baffle wall 322 is arranged on the upper magnetic buckle fitting part 321, and the upper magnetic buckle fitting part 321 includes a first groove 3211, a first limit step 3212 and a second groove 3213 that are arranged in sequence. The first vertical baffle wall 323 is arranged on one end of the transverse baffle wall 322. The second vertical baffle wall 324 is arranged on the other end of the transverse baffle wall 322 and symmetrical to the first vertical baffle wall 323. Herein, the first vertical baffle wall 323 and the second vertical baffle wall 324 are gradually increased in height along one end close to the transverse baffle wall 322.

It is understandable that the transverse baffle wall 322, the first vertical baffle wall 323 and the second vertical baffle wall 324 are combined to limit the upper magnetic buckle 40. When the upper magnetic buckle 40 and the lower magnetic buckle 30 are magnetically connected, the upper magnetic buckle 40 is adsorbed onto the upper magnetic buckle fitting part 321. Further, the transverse baffle wall 322, the first vertical baffle wall 323 and the second vertical baffle wall 324 are arranged as a U shape.

In some other embodiments, one ends of the first vertical baffle wall 323 and the second vertical baffle wall 324 away from the transverse baffle wall 322 are both provided with a limit buckle 325, and the limit buckle 325 includes: a main body clamping bar 3251 and a limit clamping tooth 3252. The main body clamping bar 3251 is arranged angled with the upper magnetic buckle fitting part 321 and inclined toward the transverse baffle wall 322. The limit clamping tooth 3252 is arranged on one end of the main body clamping bar 3251 away from the upper magnetic buckle fitting part 321 and faces the transverse baffle wall 322.

It is understandable that one ends of the first vertical baffle wall 323 and the second vertical baffle wall 324 away from the transverse baffle wall 322 are both provided with a limit buckle 325, through which limit buckle 325 to clamp and fix the upper magnetic buckle 40. The main body clamping bar 3251 and the limit clamping tooth 3252 are arranged as an L shape. By arranging the main body clamping bar 3251 to be angled with the upper magnetic buckle fitting part 321 and inclined toward the transverse baffle wall 322, the capability of the limit buckle 325 is improved in limiting and fixing the upper magnetic buckle 40.

In some other embodiments, the lower magnet fixing end 33 includes a lower magnet fixing groove 331 and a plurality of reinforcement ribs 332 arranged on the periphery of the lower magnet fixing groove 331. A magnet is arranged inside the magnet fixing groove.

It is understandable that the lower magnetic buckle 30 is arranged as a fixed magnet structure, and through the arrangement of the plurality of reinforcement ribs 332, the structure strength of the lower magnet body can be improved.

In some other embodiments, the upper magnetic buckle 40 includes: an upper magnetic buckle body 41, an upper magnet fixing chamber 42, a buckling limit part 43 and an assembly limit part 44. The upper magnet fixing chamber 42 is arranged on the upper magnetic buckle body 41. The buckling limit part 43 is arranged at an area of the upper magnetic buckle body 41 corresponding to the limit clamping tooth 3252. The assembly limit part 44 is arranged at an area of the upper magnetic buckle body 41 close to the first groove 3211.

It is understandable that through the upper magnet fixing chamber 42 arranged on the upper magnetic buckle body 41, a magnet can be effectively fixed and mounted, so that the upper magnetic buckle 40 possesses a magnetic attraction force. The buckling limit part 43 is arranged to fit with the limit buckle 325, whereby clamping and fixing the upper magnetic buckle 40 and the lower magnetic buckle 30, guaranteeing the connection strength of the magnetic buckle structure 10 for the knee-joint brace. The assembly limit part is arranged to fit with the first groove 3211, whereby reducing the assembly thickness between the upper magnetic buckle 40 and the lower magnetic buckle 30. It is to be noted that when the buckling limit part 43 is clamped on the limit buckle 325, the area of the upper magnetic buckle body 41 close to the buckling limit part 43 is received in the second groove 3213, further reducing the assembly thickness between the upper magnetic buckle 40 and the lower magnetic buckle 30 and enhancing the connection strength between the upper magnetic buckle 40 and the lower magnetic buckle 30.

In some other embodiments, an edge of the upper magnetic buckle body 41 corresponding to the first vertical baffle wall 323 and the second vertical baffle wall 324, on one side along a height direction, is arranged as an arc shape.

It is understandable that by controlling an edge of the upper magnetic buckle body 41 corresponding to the first vertical baffle wall 323 and the second vertical baffle wall 324, on one side along a height direction, to be arranged as an arc shape, the buckling limit part 43 can be conveniently rotated into the limit buckle 325, whereby the upper magnetic buckle 40 can be conveniently assembled into the lower magnetic buckle 30.

In some other embodiments, the buckling limit part 43 includes: a main body clamping bar receding section 431 and a limit baffle 432. The main body clamping bar receding section 431 is clamped on the main body clamping bar 3251. The limit baffle 432 is clamped on the limit clamping tooth 3252.

It is understandable that the limit baffle 432 and the limit clamping tooth 3252 assist in restricting the upper magnetic buckle 40 and the lower magnetic buckle 30 from disengaging along the height direction, guaranteeing the connection strength between the upper magnetic buckle 40 and the lower magnetic buckle 30.

In some other embodiments, the assembly limit part 44 is arranged as a convex plate structure that is clamped to the second groove 3213.

It is understandable that the assembly limit part 44 is arranged as a convex plate structure so that the assembly limit part 44 can achieve some auxiliary fixation while being fitted into the second groove 3213.

In some specific embodiments, an S-pole magnet 50 is arranged inside the upper magnetic buckle 40 while an N-pole magnet 60 is arranged inside the lower magnetic buckle 30, or, an N-pole magnet 60 is arranged inside the upper magnetic buckle 40 while an S-pole magnet 50 is arranged inside the lower magnetic buckle 30. The magnets in both the upper magnetic buckle 40 and the lower magnetic buckle 30 are fixed by gluing. The upper magnetic buckle body 41 is formed with bandage spacings 45 between the upper magnet fixing chamber 42, the buckling limit part 43 and the assembly limit part 44. A bandage can be arranged in the bandage spacings 45, through which bandage the upper magnetic buckle 40 can be lifted up, so that the upper magnetic buckle 40 is separated from the lower magnetic buckle 30, whereby facilitating the removal of the knee-joint brace.

A second embodiment of the present disclosure provides a knee-joint brace, including the magnetic buckle structure 10 for the knee-joint brace described in the first embodiment of the present disclosure. It is understandable that by employing the magnetic buckle structure 10 for the knee-joint brace provided in the first embodiment of the present disclosure, the knee-joint brace provided in the present embodiment can magnetically fix or replace the bandage of the knee-joint brace due to the arrangement of the upper magnetic buckle 40 and the lower magnetic buckle 30, whereby being convenient for a user to wear and remove the knee-joint brace.

To sum up, the present disclosure provides a magnetic buckle structure for a knee-joint brace and a knee-joint brace having the same. The magnetic buckle structure for the knee-joint brace includes a joint brace body, a lower magnetic buckle arranged on the joint brace body, and an upper magnetic buckle arranged on the lower magnetic buckle and magnetically connected to the lower magnetic buckle. It is understandable that through the arrangement of the upper magnetic buckle and the lower magnetic buckle, a bandage of the knee-joint brace can be magnetically fixed or replaced, whereby being convenient for a user to wear and remove the knee-joint brace.

It should be understood that the application of the present disclosure is not limited to the above examples. For the ordinary staff in this field, improvements or variations may be made according to the above description, and these improvements or variations are intended to be included within the scope of protection of the claims appended hereinafter.

What is claimed is:

1. A magnetic buckle structure for a knee-joint brace, comprising:
- a joint brace body;
- a lower magnetic buckle arranged on the joint brace body; and
- an upper magnetic buckle arranged on the lower magnetic buckle and magnetically connected to the lower magnetic buckle;
- wherein the lower magnetic buckle comprises;
  - a lower magnetic buckle body integrally formed with the joint brace body;
  - an upper magnetic buckle connection end arranged on an upper end surface of the lower magnetic buckle body along a height direction;
  - wherein the upper magnetic buckle connection end comprises:
  - an upper magnetic buckle fitting part arranged on the upper end surface of the lower magnetic buckle body along the height direction;
    - a transverse baffle wall arranged on the upper magnetic buckle fitting part;
    - a first vertical baffle wall arranged on a first end of the transverse baffle wall; and
    - a second vertical baffle wall arranged on a second end of the transverse baffle wall and symmetrical to the first vertical baffle wall;
    - wherein the first vertical baffle wall and the second vertical baffle wall are gradually increased in height extending away from the transverse baffle wall.

2. The magnetic buckle structure for the knee-joint brace according to claim 1, wherein the lower magnetic buckle comprises:
- a lower magnet fixing end arranged on a lower end surface of the lower magnetic buckle body along the height direction.

3. The magnetic buckle structure for the knee-joint brace according to claim 2, wherein
- the upper magnetic buckle fitting part comprising a first groove, a first limit step and a second groove that are arranged in sequence.

4. The magnetic buckle structure for the knee-joint brace according to claim 3, wherein the first vertical baffle wall and the second vertical baffle wall opposite the transverse baffle wall are both provided with a limit buckle, and the limit buckle comprises:
- a main body clamping bar arranged angled with the upper magnetic buckle fitting part and inclined toward the transverse baffle wall; and
- a limit clamping tooth arranged on one end of the main body clamping bar away from the upper magnetic buckle fitting part and facing the transverse baffle wall.

5. The magnetic buckle structure for the knee-joint brace according to claim 4, wherein the upper magnetic buckle comprises:
- an upper magnetic buckle body;
- an upper magnet fixing chamber arranged on the upper magnetic buckle body;
- a buckling limit part arranged at a first area of the upper magnetic buckle body corresponding to the limit clamping tooth; and
- an assembly limit part arranged at a second area of the upper magnetic buckle body close to the first groove.

6. The magnetic buckle structure for the knee-joint brace according to claim 5, wherein
- an edge of the upper magnetic buckle body corresponding to the first vertical baffle wall and the second vertical baffle wall, along a height direction, is arranged as an arc shape.

7. The magnetic buckle structure for the knee-joint brace according to claim 5, wherein the buckling limit part comprises:
- a main body clamping bar receding section clamped on the main body clamping bar; and
- a limit baffle clamped on the limit clamping tooth.

8. The magnetic buckle structure for the knee-joint brace according to claim 5, wherein the assembly limit part is arranged as a convex plate structure that is clamped to the second groove.

9. The magnetic buckle structure for the knee-joint brace according to claim 4, wherein the lower magnet fixing end comprises a lower magnet fixing groove and a plurality of reinforcement ribs arranged on a periphery of the lower magnet fixing groove; and a magnet is arranged inside the magnet fixing groove.

10. A knee-joint brace, comprising a magnetic buckle structure, wherein the magnetic buckle structure comprises:

a joint brace body;

a lower magnetic buckle arranged on the joint brace body; and an upper magnetic buckle arranged on the lower magnetic buckle and magnetically connected to the lower magnetic buckle;

wherein the lower magnetic buckle comprises;

a lower magnetic buckle body integrally formed with the joint brace body;

an upper magnetic buckle connection end arranged on an upper end surface of the lower magnetic buckle body along a height direction;

wherein the upper magnetic buckle connection end comprises:

an upper magnetic buckle fitting part arranged on the upper end surface of the lower magnetic buckle body along the height direction;

a transverse baffle wall arranged on the upper magnetic buckle fitting part;

a first vertical baffle wall arranged on a first end of the transverse baffle wall; and a second vertical baffle wall arranged on a second end of the transverse baffle wall and symmetrical to the first vertical baffle wall;

wherein the first vertical baffle wall and the second vertical baffle wall are gradually increased in height extending away from the transverse baffle wall.

* * * * *